(12) United States Patent
Sellergren et al.

(10) Patent No.: US 9,329,186 B2
(45) Date of Patent: May 3, 2016

(54) IMPRINTED POLYMERS WITH AFFINITY FOR PHOSPHORYLATED PEPTIDES AND PROTEINS

(75) Inventors: Börje Sellergren, Schwerte (DE); Marco Emgenbroich, Neuss (DE); Andrew J. Hall, Kent (GB)

(73) Assignee: MIP Technologies AB (SE)

( * ) Notice: Subject to any disclaimer, the term of this patent is extended or adjusted under 35 U.S.C. 154(b) by 988 days.

(21) Appl. No.: 12/742,377

(22) PCT Filed: Nov. 11, 2008

(86) PCT No.: PCT/SE2008/051290
§ 371 (c)(1),
(2), (4) Date: Sep. 14, 2010

(87) PCT Pub. No.: WO2009/064245
PCT Pub. Date: May 22, 2009

(65) Prior Publication Data
US 2011/0015373 A1 Jan. 20, 2011

(30) Foreign Application Priority Data

Nov. 12, 2007 (SE) ...................... 0702512

(51) Int. Cl.
| G01N 33/68 | (2006.01) |
| --- | --- |
| B01D 15/38 | (2006.01) |
| B01J 20/26 | (2006.01) |
| C07K 1/22 | (2006.01) |

(52) U.S. Cl.
CPC ........ *G01N 33/6812* (2013.01); *B01D 15/3852* (2013.01); *B01J 20/268* (2013.01); *C07K 1/22* (2013.01); *G01N 2600/00* (2013.01)

(58) Field of Classification Search
None
See application file for complete search history.

(56) References Cited

U.S. PATENT DOCUMENTS

| 6,870,021 | B2 * | 3/2005 | Sellergren | ............... | C07B 57/00 526/199 |
| --- | --- | --- | --- | --- | --- |
| 7,208,557 | B2 * | 4/2007 | Sellergren | ............... | C07B 57/00 526/199 |
| 7,332,553 | B2 * | 2/2008 | Sellergren | ............... | C07B 57/00 526/199 |
| 2004/0058006 | A1 | 3/2004 | Barry et al. | | |
| 2008/0064810 | A1 * | 3/2008 | Sellergren et al. | ............. | 524/555 |
| 2009/0081145 | A1 * | 3/2009 | Knorr et al. | ................. | 424/70.1 |
| 2010/0203001 | A1 * | 8/2010 | Knorr et al. | ................ | 424/70.51 |
| 2011/0015373 | A1 * | 1/2011 | Sellergren et al. | ............. | 530/344 |

FOREIGN PATENT DOCUMENTS

| WO | WO-99/19276 A2 | 4/1999 |
| --- | --- | --- |
| WO | WO-01/61355 A1 | 8/2001 |
| WO | WO-2006/041370 A1 | 4/2006 |
| WO | WO-2006/041398 A1 | 4/2006 |
| WO | WO2006041370 | * 4/2006 ............. C08F 12/08 |
| WO | WO-2007/123708 A2 | 11/2007 |

OTHER PUBLICATIONS

Emgenbroich, M., et al., "A Phosphotyrosine-Imprinted Polymer Receptor for the Recognition of Tyrosine Phosphorylated Peptides", Chem. Eur. J., 14('31), (2008), 9516-9529.*
"International Application Serial No. PCT/SE2008/051290, International Serial Report mailed Feb. 20, 2009", 7 pgs.
"International Application Serial No. PCT/SE2008/051290, Written Opinion mailed Feb. 20, 2009", 6 pgs.
"European Application Serial No. 08850445.1, Supplementary Europeam Search Report dated Nov. 25, 2010", 9 pgs.
Bühlmann, P., et al., "Strong Hydrogen Bond-Mediated Complexation of $H_2PO_4$ by Neutral Bis-Thiourea Hosts", *Tetrahedron*, 53(5), (1997), 1647-1654.
Emgenbroich, M., et al., "A Phosphotyrosine-Imprinted Polymer Receptor for the Recognition of Tyrosine Phosphorylated Peptides", *Chem. Eur. J.*, 14(31), (2008), 9516-9529.
Etter, M. C., et al., "1,3-Bis(*m*-nitrophenyl)urea: An Exceptionally Good Complexing Agent for Proton Acceptors", *J. Am. Chem. Soc.*, 110, (1988), 5896-5897.
Fan, E., et al., "Molecular Recognition: Hydrogen-Bonding Receptors That Functions in Highly Competitive Solvents", *J. Am. Chem. Soc.*, 115, (1993), 369-370.
Gomez, D. E., et al., "Urea vs. thiourea in anion recognition", *Org. Biomol. Chem.*, 1495-1500.
Hall, A. J, et al., "Urea Host Monomers for Stoichiometric Molecular Imprinting of Oxyanions", *Journal of Organic Chemistry*, 70(5), (2005), 1732-1736.
Manesiotis, P., et al., "An enantioselecitve imprinted receptor for Z-glutamate exhibiting a binding induced color change", *Chem. Commun.*, (2004), 2278-2279.
Nishino, H., et al., "Selective Protein Capture by Epitope Imprinting", *Angew. Chem. Int. Ed.*, 45, (2006), 2392-2396.
Ojida, A., et al., "Molecular Recognition and Fluorescence Sensing of Monophosphorylated Peptides in Aqueous Solution by Bis(zinc(II)-dipicolylamine)-Based Artificial Receptors", *J. Am. Chem. Soc.*, 126, (2004), 2454-2463.
Sajonz, P., et al., "Study of the thermodynamics and mass transfer kinetics of two enantiomers", *Journal of Chromatography A*, 810, (1998), 1-17.
Titirici, M. M., et al., "Heirarchical Imprinting Using Crude Peptide Solid Phase Synthesis Products as Templates", *Chem. Mater.* 15(4) (2003), 822-824.
Turner, N. W., et al., "From 3D to 2D: A Review of the Molecular Imprinting of Proteins", Biotechnol. Prog., 22(6), (2006), 1474-1489.
Urraca, J. L., et al., "A Stoichiometric Molecularly Imprinted Polymer for the Class-Selective Recognition of Antibiotics in Aqueous Media", *Angew. Chem. Ind. Ed.*, 45, (2006), 5158-5161.

* cited by examiner

*Primary Examiner* — Maury Audet
(74) *Attorney, Agent, or Firm* — Schwegman, Lundberg & Woessner, P.A.

(57) ABSTRACT

The present invention relates to a method of separating or extracting phosphorylated amino acids, peptides or proteins with a molecularly imprinted polymer and to the preparation of said molecularly imprinted polymer as well as use of a molecularly imprinted polymer for separating or extracting phosphorylated amino acids, peptides or proteins.

9 Claims, 7 Drawing Sheets

Fig. 1

ALGADDS<u>Y</u>YTAR

ALGADDS<u>Y</u>YTAR
<u>P</u>

1. P or no P

ALGADD<u>S</u>YYTAR
P

ALGADDS<u>Y</u>YTAR
<u>P</u>

2. pTyr or pSer

ALGADDSY<u>Y</u>TAR
<u>P</u>

ALGADDS<u>Y</u>YTAR
<u>P</u>

3. Regioselectivity

ALGADDS<u>YY</u>TAR
<u>P</u>

ALGADDS<u>YY</u>TAR
<u>PP</u>

4. Stoichiometry

US 9,329,186 B2

IMPRINTED POLYMERS WITH AFFINITY FOR PHOSPHORYLATED PEPTIDES AND PROTEINS

RELATED APPLICATIONS

This application is a U.S. National Stage Filing under 35 U.S.C. 371 from International Patent Application Serial No. PCT/SE2008/051290, filed Nov. 11, 2008, and published on May 22, 2009 as WO 2009/064245 A1, which claims the priority benefit of Sweden Application Serial No. 0702512-5, filed Nov. 11, 2007, the contents of which applications and publication are incorporated herein by reference in their entirety.

TECHNICAL FIELD OF THE INVENTION

The present invention relates to a method for extracting or separating phosphorylated amino acids, peptides and proteins and use of said method.

BACKGROUND OF THE INVENTION

Protein phosphorylation and dephosphorylation is a key regulating mechanism of biological processes and therefore a post-translational modification of profound biological importance. It is of critical importance in intracellular signal transduction processes where defects in the kinase-phosphatase switch have been implicated as an important mechanism in several disease processes, including cancer.

The main phosphorylated amino acid residues formed by post-translational modifications are the following

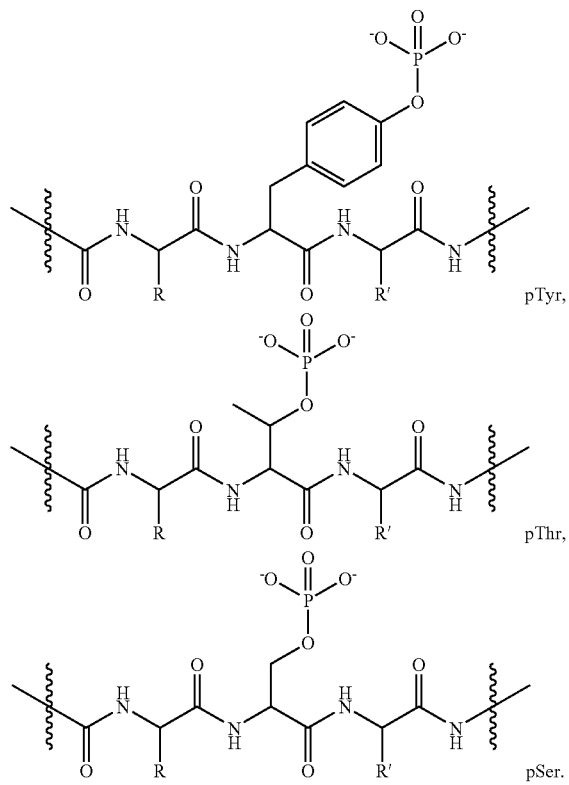

A need has emerged in the Life Sciences for means to selectively extract phosphorylated peptides or proteins. Protein purification is one example where removal of phosphorylated biproducts presents serious challenges. Mapping of the phosphoproteome (defined here as the complete cellular repertoire of phosphorylated proteins and peptides) is an important objective. Apart from a fundamental understanding of disease processes, the objectives can be to identify and characterise new drug targets, to evaluate the efficacy of new drugs or to identify biomarkers for disease leading to new diagnostic tools.

In this context it has proven particularly difficult to obtain a comprehensive picture of the phosphorylated protein landscape due to the low abundance or difficulties in enrichment of such proteins from biological extracts or digests. In particular, proteins and peptides phosphorylated at tyrosine residues constitute a challenging analytical problem. As tyrosine phosphorylation is a sub-stoichiometric modification often occurring in low-abundance proteins, the presently used separation and detection techniques based on antibodies or chelating chromatographic materials often exhibit insufficient selectivity and sensitivity to allow the modified proteins to be individually determined. Thus, there is a general need for techniques capable of separating or sensing common structures in proteins or peptides. Apart from the need for a generic fractionation tool capable of isolating all pTyr-containing peptides over non-phosphorylated peptides and peptides phosphorylated at Ser (serine) or Thr (threonine), other levels of selectivity are equally important (FIG. 1). In addition to the need for pSer (phosphorylated serine) and pThr (phosphorylated threonine) selectivities, where also dedicated fractionation tools are needed, receptors that can recognize the amino acid sequence around the phosphorylation site would find use in diagnostic applications once reliable biomarkers have been identified. Such receptors could be incorporated in sensors where the binding event would be translated into a measurable signal. For instance, binding can give rise to a change in colour or luminescence of a receptor which could be easily measured.

Alternatively, such receptors if prepared in soluble or nanoparticulate form could be used as therapeutic agents e.g. inhibiting dephosphorylation events or as imaging agents provided that the receptor contains a visible label.

Several attempts to complex phosphorylated peptides have been based on low molecular weight artificial receptors but they often exhibit a charge dependent sequence bias due to their charged nature and hence preference for complementary charged amino acids. Neural receptors containing no charge bias would be more interesting in this regard. In this area molecularly imprinted polymers could play an important role, complementing currently used immunological and chemical methods.

Molecular imprinting has resulted in a range of robust polymer-based receptors (known as MIPs), predominantly for small lipophilic target molecules. The technique entails copolymerisation of mono- and di-functional monomers in the presence of a template, which is thereafter removed to leave sites that can be reoccupied by the template or closely related compounds. Vis-á-vis biological receptors, MIPs are distinguished by their robustness and ease of synthesis, which has led to their use in a range of molecular recognition based applications targeting small molecules.

While MIPs have proven their value for the enrichment of low molecular weight analytes, their use in the enrichment of peptide or protein target molecules has met with limited success.[1] However, this may change by the use of epitopes of the target protein in question as templates. Striking affinities and selectivities have been observed for peptides[2] and proteins[3] using polymers imprinted with shorter peptide sequences derived from the N- or C-termini of the target proteins or peptides.

SUMMARY OF THE PRESENT INVENTION

The present invention discloses an artificial phosphoprotein or phosphopeptide receptor, featuring a tight binding site for phosphotyrosine.

In a second embodiment the invention discloses an artificial phosphoprotein or phosphopeptide receptor, featuring a tight binding site for phosphoserine.

In a third embodiment the invention discloses an artificial phosphoprotein or phosphopeptide receptor, featuring a tight binding site for phosphothreonine.

In a forth embodiment the invention discloses artificial phosphoprotein or phosphopeptide receptors capable of preferentially binding such targets exhibiting a specific amino acid sequence linked to the phosphorylated amino acid pTyr, pSer or pThr.

The invention also discloses the use of above receptors for extracting phosphorylated peptides or proteins from mixtures. These can serve as fractionation tools in proteomics or as affinity phases for purifying peptides or proteins.

The invention may additionally be used in medical therapy, wherein the receptors (Molecularly imprinted polymers, MIPs) is used to extract or separate phosphorylated peptides or proteins from biological fluids e.g. based on apheresis or as oral adsorbers.

Additionally, the receptors in nanoparticulate may be used as therapeutic agents e.g. for modulating a biological activity by e.g. depletion of phosphorylated peptides or proteins or by inhibiting dephosphorylation events or as imaging agents provided that the receptor contains a visible label.

The invention also discloses the use of above receptors in diagnostics. This can be for analysing single or an array of biomarkers possibly simultaneously. The latter can be performed in an SPE (solid phase extraction) format using the receptors as biomarker-specific sorbents or in assay formats e.g. competitive assays. Alternatively the receptors may be incorporated into sensors where the binding event would be translated into a measurable signal. For instance, in optical sensors binding can give rise to a change in color or luminescence of the receptor which could be measured.

The invention also discloses such receptors prepared in soluble form which can potentially be used as therapeutic agents inhibiting dephosphorylation events or as imaging agents provided that the receptor contains a visible label.

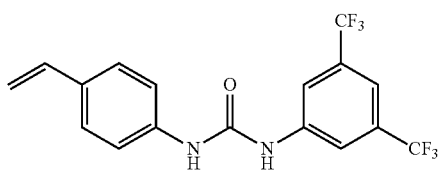

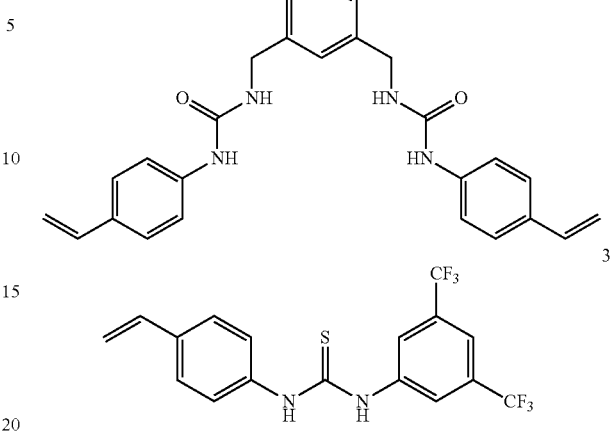

The aforementioned receptors are obtained by molecular imprinting leading to imprinted polymers. These are preferably obtained from diarylurea host monomers (for examples see monomers 1, 2 and 3),[4,5] designed to bind oxyanions, in combination with N and/or O protected phosphotyrosine templates.

In one embodiment the receptor may be used in optical sensors, wherein the change in color or luminescence upon binding to the receptors may be caused by a chromophore or luminescent substituent built into a host monomers However, in addition to the urea-based monomers, other monomers can be used which exhibit affinity for the phosphate group. These are non-exclusively nitrogen basic monomers (e.g. amines, amidines, guanidines), hydrogen bonding (e.g. ureas), metal ion-complexing monomer, monomers containing quarternary ammonium groups etc. may be used for imprinting in the imprinting step. Examples of commodity monomers that may be used include: 2- or 4-vinylpyridin (VPY), N,N-diethylaminoethylmethacrylate (DEAEMA), N,N,N-trimethyl-N-4-vinylbenzylammonium chloride, methacrylic acid (MAA), acrylic acid, acrylamide, methacrylamide (MAAM), vinylpyrrolidone, styrene, cyanostyrene, acrylonitrile, 2-hydroxyethylmethacrylate, vinylimidazole.

In one embodiment the invention allows potent receptors for modified peptides to be prepared using a single amino acid or a single amino acid derivative as a template.

The present invention also relates to a method of separating or extracting a phosphorylated amino acid, peptide or protein comprising providing a molecularly imprinted polymer obtainable by providing at least one monomer exhibiting affinity for phosphate groups at least one template selected from templates exhibiting phosphate groups or groups isosteric to phosphate groups and at least one cross-linker, forming a pre-polymerization mixture, and polymerizing said pre-polymerization mixture;

contacting said molecularly imprinted polymer with a mixture containing at least one amino acid, peptide, protein or a mixture thereof, wherein at least one of said at least one amino acid, peptide or protein or any mixture thereof is a phosporylated amino acid, peptide, protein or any mixture thereof and is captured by the molecularly imprinted polymer.

The present invention also relates to use of a molecularly imprinted polymer obtainable by providing at least one monomer, at least one template selected from templates exhibiting phosphates groups or groups isosteric to phosphate groups and at least one cross-linker, forming a pre-polymerization mixture, and polymerizing said pre-polymerization mixture; for separating or extracting a phosphorylated amino acid, peptide or protein, wherein said molecularly imprinted polymer is contacted with a mixture containing at least one amino acid, peptide, protein or a mixture thereof, wherein at least one of said at least one amino acid, peptide or protein or any mixture thereof is phosporylated.

In some aspects of the invention the method additionally comprises releasing the captured phosphorylated amino acid peptide or protein from said molecularly imprinted polymer.

In some aspects of the invention the mixture may contain two or more amino acids, peptides, or proteins or a mixture thereof; or the mixture may contain at least one amino acid, peptide or protein that is phosphorylated and at least one amino acid, peptide or protein that is non-phosphorylated.

In some aspects of the invention the template may be selected from a single amino acid, which may be decorated with oligomers or polymers. In some aspects the template is N and/or O-protected phosphotyrosine or a salt thereof. In some aspects the template is N,O protected phosphotyrosine or a salt thereof.

In some aspects of the invention the monomer is selected from a 1,3-disubstituted urea or thiourea; or 1,3-diarylsubstituted urea or thiourea, such as compounds 1, 2 or 3.

In some aspects of the invention a phosphorylated peptide or protein is selectively extracted or separated over other phosphorylated or non-phosphorylated peptides or protein. In particular aspects of the invention the phosphorylated peptide or protein is a peptide or protein phosphorylated on one type of amino acid side chain.

In some aspects of the invention phosphorylated tyrosine, or peptides or proteins containing phosphorylated tyrosine are selectively separated or extracted over phosphorylated or non-phosphorylated serine or peptides or proteins containing phosphorylated or non-phosphorylated serine and/or phosphorylated or non-phosphorylated threonine or peptides or proteins containing phosphorylated or non-phosphorylated threonine.

In some aspects the invention relates to the use of the above mentioned methods in diagnostics, assays, sensors, in solid phase extraction, in protein purification or medical therapy, such as separation, depletion or extraction of a phosphorylated amino acid, peptide or protein from biological fluids.

SHORT DESCRIPTION OF THE DRAWINGS

FIG. 1 illustrates different levels of phosphopeptide discrimination in the design of pTyr-imprinted polymers.

FIG. 2 schematically illustrates the pre-polymerization complexes formed between monourea monomer 1 and receptor monomer 2 with Fmoc-pTyrOMe and procedure for preparation of the corresponding imprinted polymers.

FIG. 3 discloses retention factors for the amino acid analytes on columns packed with the imprinted and non-imprinted control polymers.

FIG. 4 discloses retention factor for Fmoc-pTyrOMe using MeCN/[potassium phosphate buffer, 0.02 M, pH 7]: 50/50 (v/v) as mobile phase FIG. 5 schematically illustrates the imprinting discussed in the detailed description.

DETAILED DESCRIPTION OF THE PRESENT INVENTION 1,3 disubstituted ureas have long been exploited as (charge) neutral hosts for complexing oxyanion guests.[6,7] They establish cyclic hydrogen bonds acting as a twofold donor to the acceptor e.g. carboxylate, phosphate or sulphonate. The affinity for the guest increases with the acidity of the urea protons (donor ability) but is also related to the ability of the host to self-associate (poor acceptor ability) and thereby influence its solubility.[8] Commonly, thioureas are used in the host design because they are more acidic and more soluble than ureas and, thus, form stronger hydrogen bonds with a given acceptor.[7] We previously found that the polymerizable 1,3-diaryl urea 1 displayed a binding constant of ca. 8800 M$^{-1}$ towards TBA-benzoate in DMSO[9] which is in agreement with other reported diarylurea receptors[7]. The monomers could be used to imprint carboxylates resulting in polymers recognizing the guest with high affinity and selectivity in water rich media.[5]

Also, these monomers can be designed to exhibit a change in color or luminescence upon binding of the guest, a feature which may be favorably used in the design of chromogenic sensors for the guests e.g. for phosphorylated peptides or proteins in biomarker sensors or similar.

Figure 3:
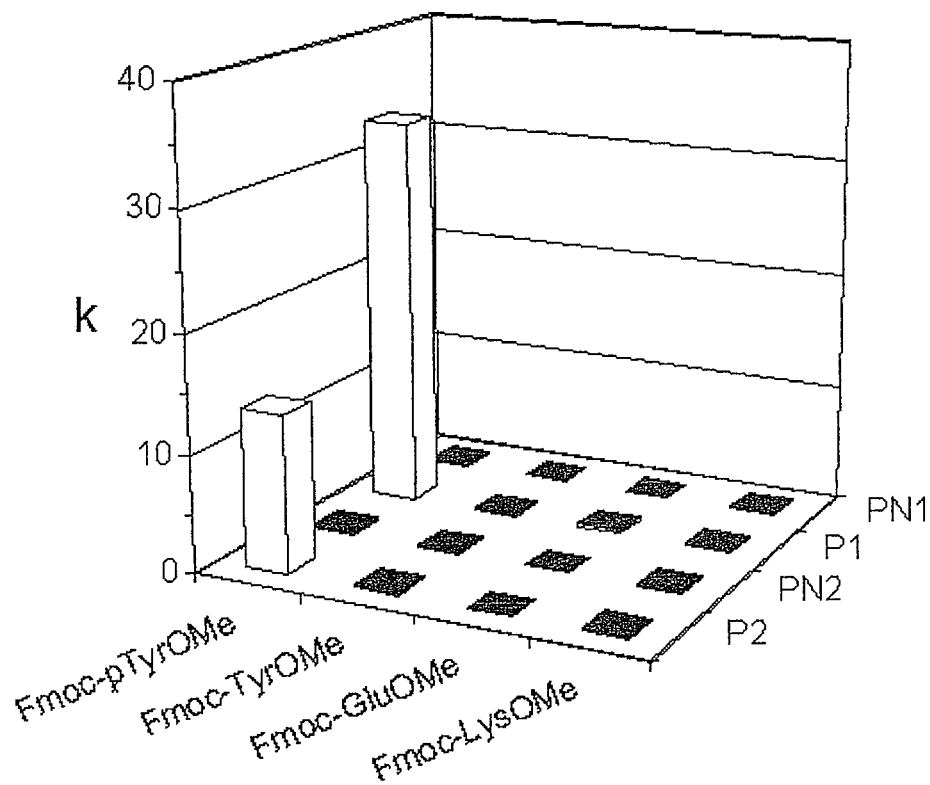

As a first step in our evaluation of hosts for complexing phosphate we thus decided to compare this host monomer with the supposedly more potent thiourea version 3 (FIG. 3). Monomer 3 was synthesised analogously to the urea version in one step by adding aminostyrene to 3,5-bistrifluorophenylthiocyanate. Mono- or Bis-tetrabutylammonium 1-naphtyl phosphate was chosen as guest mimicking the phenylphosphate substituent of the template, Fmoc-pTyrOMe. The receptor monomer solutions (1 mM in $d_6$-DMSO) were titrated with a standard solution of the anion guest up to a ten-fold molar excess. Table 1 shows the complexation induced shifts (CIS) of the protons used to calculate the given binding constants (K) and the complex stoichiometries determined by Job's method of continuous variation or obtained from other sources.[10]

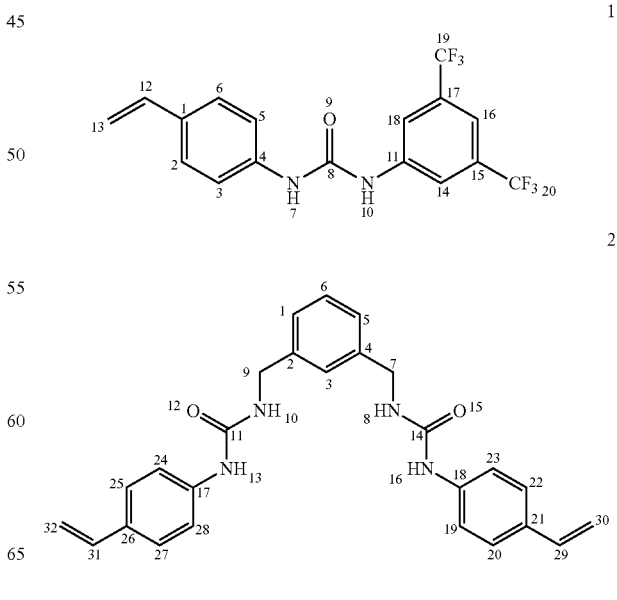

TABLE 1

Association constants, stoichiometries and complexation induced shifts for complexes formed between urea host monomers and phosphate guests in $d_6$-DMSO.

| Host monomer | Guest | Proton | K (M$^{-1}$)$^a$ | Complex (H:G) | CIS$^a$ |
|---|---|---|---|---|---|
| 1 | TBANP* | NH (7, 10) | 2675 ± 325 | 1:1 | 3.31 |
| 1 | TBA$_2$NP** | CH (13) | >10000$^b$ | 2:1 | 0.14 |
| 2 | TBA$_2$NP | CH (6) | 2924 ± 898 | 1:1 | 0.20 |
|   |   | NH (13, 16) | n.d. |   | 3.43 |
| 3 | TBANP | NH (7, 10) | 1089 ± 120 | 1:1 | 1.53 |
| 3 | TBA$_2$NP | CH (13) | >10000$^b$ | 2:1 | 0.23 |

*TBANP is tetrabutylammonium 1-naphtyl hydrogen phosphate
**TBA$_2$NP is bistetrabutylammonium 1-naphtyl phosphate
$^a$Average binding constants (K) and complexation induced shifts (CIS) based on the shift values of the resonance signals indicated unless given separately.
$^b$Low estimate representing the inverse of the lowest concentration of free ligand giving host saturation. The two binding sites of the divalent NP was assumed to interact identically and independently with the urea host monomer 1.

The titration was accompanied by pronounced downfield shifts of the urea protons, together with significant shifts for all remaining protons. The signals that could be monitored throughout the titration were used to calculate free and bound concentrations and, if possible, the association constants from the resulting binding curve obtained via nonlinear regression.

Considering first the relative complex stabilities involving monoureas 1 and 3, the mono-tetrabutylammonium salt (TBANP) was used as a monoanion guest in order to uniquely promote formation of 1:1 complexes. After having confirmed the 1:1 stoichiometry from the Job's plots, the 1:1 binding model was used in order to determine the respective association constants. Surprisingly, the oxourea monomer formed the more stable complexes (K=2675 M$^{-1}$), more than twofold stronger than the corresponding thiourea complexes (K=1089M$^{-1}$).

We then went on to assess the urea receptor monomer 2 which previously have been used as phosphate receptor.[11] Being designed for complexing the dianion we tested its ability to complex TBA$_2$NP. Although displaying the expected 1:1 stoichiometry, the binding curves exhibited a slight sigmoidal shape and were not well fitted with the 1:1 binding model. Nevertheless, the corresponding association constant is given in Table 1 assuming the latter model as a best approximation. In spite of the ability of this receptor to donate four converging hydrogen bonds to the phosphate dianion guest, the urea protons are less acidic and hence the estimated association constant (K=2924M−1) only slightly exceeds that of the twofold hydrogen bonded complex between 1 and TBANP.

Higher complexes between 1 and phosphate could thus be expected to define tighter phosphate receptors if templated into a polymer and we therefore studied the monoureas with respect to their abilities to complex the dianion TBA$_2$NP. Due to difficulties in removing residual methanol from TBA$_2$NP, the urea protons could not always be clearly distinguished throughout the titration, although the maximum shifts (CIS) were in agreement with literature values for similar hosts. The vinyl protons, however, leveled off at 2:1 host-guest stoichiometry and the very low free concentrations allowed only a minimum value of K of 10000M$^{-1}$ to be estimated. The thiourea host 3 again displayed a somewhat shallower curve, which was also in agreement with the differencies observed when in situ deprotonation was attempted using triethylamine as base. Using this weaker base, ion pairing is competing with the urea complexation leading to significantly weaker complexes and a 1:1 host guest stoichiometry. On the basis of the titration results, we decided to include 1 and 2 as functional monomers for imprinting the phosphate template.

Molecular modelling of the host guest complexes was performed using the genetic algorithm-based FlexiDock™ programme for docking ligands into receptor active sites. This programme works on a receptor/ligand pair where the receptor backbone atoms are fixed in space, but the ligand is mobile (rotation/translation can be applied). The modelling gave minimum energy complex geometries and their relative interaction energies, the latter having no physical meaning but for ranking purpose only. The lowest energy complex for Fmoc-pTyrOMe and 1, with a FlexiDock™ interaction energy of −544 kcal/mol, features the bistrifluoromethylphenyl substituents of both urea ligands pointing in the same direction allowing four strong hydrogen bonds to develop and with the styryl substituent of one of the ligands placed at π-stacking distance from the tyrosine phenyl group. This arrangement should result in a tight cavity complementary to the phenylphosphate group of pTyr. On the contrary, the corresponding complex with 2 is poorly defined resulting in a FlexiDock energy of only −252 kcal/mol. The orientation prevents all urea protons in engaging in hydrogen bonding with the phosphate. Thus, the modelling results confirmed the stability data obtained from the $^1$H-NMR titrations.

Functional monomers exhibiting affinity for the phosphate group e.g. nitrogen basic monomers (e.g. amines, amidines, guanidines), hydrogen bonding (e.g. ureas), metal ion-complexing monomer, monomers containing quarternary ammonium groups etc. may be used for imprinting in the imprinting step. Examples of commodity monomers that may be used include: 2- or 4-vinylpyridin (VPY), N,N-diethylaminoethylmethacrylate (DEAEMA), N,N,N-trimethyl-N-4-vinylbenzylammonium chloride, methacrylic acid (MAA), acrylic acid, acrylamide, methacrylamide (MAAM), vinylpyrrolidone, styrene, cyanostyrene, acrylonitrile, 2-hydroxyethylmethacrylate, vinylimidazole.

However, having established the potency of the urea monomers to complex phosphates we turned our attention to the polymer preparation. Templates exhibiting phosphates or groups isosteric to the phosphate groups may be used to target phosphorylated biomolecules. In order to create additional discrimination, the phosphate group may be covalently bound to an aryl group for pTyr selectivity or an aliphatic hydroxyl group for pSer or pThr selectivity. In order to provide a site complementary to a larger molecule e.g. peptide or protein, the template may be decorated with void creating substitutents e.g. oligomers or polymers (e.g. polyethylenglycol) which can be dentritic or hyperbranced in structure. The phosphate template may further be bound to a protein which in analogy of antigens used to elicit immunogenic response, may be used as template for generating an imprinted polymer.

Figure 2:
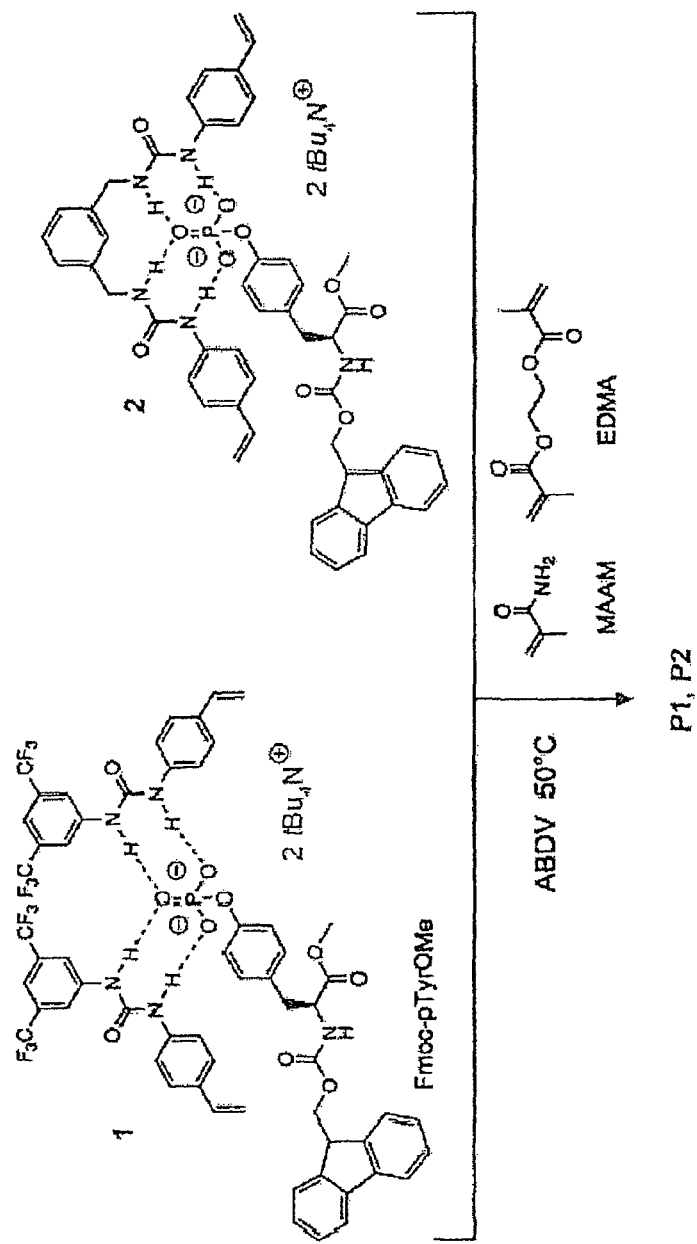

In one example the template for pTyr selective receptors was Fmoc-pTyrOMe where the phosphate group is linked to the 4-position of the phenyl group of Fmoc-PheOMe. This was first synthesized from Fmoc-TyrOMe and POCl$_3$ as described in the experimental section. Given the high affinity displayed by in particular monomer 1 towards naphtylphosphate in the competitive solvent DMSO, we expected a quantitative complexation of the template under the imprinting conditions used. Polymers P1 and P2 and the corresponding non-imprinted polymers were thus prepared using monomer 1 and 2 in a 2:1 and 1:1 stoichiometric ratio to the template Fmoc-pTyrOMe as disclosed in FIG. 2.

Methacrylamide was added as a supplementary monomer to provide additional hydrogen bond stabilization and all monomers polymerized via free radical initiation, with ethylene glycol dimethacrylate (EDMA) as crosslinking monomer and THF (P1) or DMF (P2) as solvents. The crosslinking monomer can in principle be chosen from a vast array of alternative monomers e.g. ethylene glycol dimethacrylate (EDMA), divinylbenzene (DVB), trimethylolpropane trimethacrylate (TRIM), pentaerythritol triacrylate (PETRA), N,N'-methylene bisacrylamide (MBA), ethylenebisacrylamide, N,O-bismethacryloylethanolamine or N,O-bisacryloylethanolamine. The choice of solvent is also not limited to the above but can be any solvent capable of dissolving all components of the mixture of monomers, template and initiator. The choice here was guided by the solubility of the urea template complex in the monomer mixture. Free radical polymerization at 40° C. subsequently afforded the imprinted and non-imprinted polymers.

Alternative polymerization techniques are possible. For instance, the monomer mixture can be polymerized via photoinitiation instead of thermal initiation, it can be grafted on the surface of a carrier or support e.g. porous beads, planar substrates or in situ on the surface of a flow through monolithic support inside a column. Further formats include suspension or emulsion polymerization, precipitation or dispersion polymerization or miniemulsion polymerization. These techniques may allow the synthesis of nanoparticles of controlled average size and dispersity. Radical polymerization under controlled conditions via atom transfer radical polymerization (ATRP), reversible addition fragmentation chain transfer polymerization (RAFT) or nitroxide-mediated polymerization may lead to improved properties of the polymer receptors in particular in the context of grafting. Combining the procedure outlined in FIG. 2 with means to produce micro- or nano-gels may lead to soluble or nanoparticulate imprinted polymers which may find important applications as imaging or therapeutic agents.

The polymers were crushed and sieved to a 25-36 μm particle size fraction and then subjected to template removal by washing with acidic methanol followed by extraction with methanol using a Soxhlet apparatus. Based on elemental analysis data of remaining phosphorous in the polymers (Table 3), more than 95% of the template was removed by this treatment. In order to investigate whether the imprinted and control polymers were otherwise comparable in terms of morphology and composition the polymers were characterised by elemental analysis, XPS, IR-spectroscopy, $^{13}$C-CP-MAS NMR and nitrogen sorption analysis. Elemental analysis showed slightly lower carbon contents of all materials, possibly related to their hygroscopic nature, but reasonable agreement with the theoretical concentrations for the other elements. XPS is used for quantitative analysis of surface compositions but typically poorly reflects the overall polymer composition. Nevertheless, for all elements except carbon the agreement between the XPS results and the theoretical composition was evident and did not indicate any compositional difference between the imprinted and non-imprinted polymers.

Only the nitrogen sorption technique, which shows the porous properties of the materials, gave evidence for differencies between imprinted and non-imprinted polymer (Table 2).

TABLE 2

Physical properties of Fmoc-pTyrOMe imprinted and non-imprinted polymers

| Polymer | S (m$^2$/g) | V$_p$ (mL/g) | D$_p$ (nm) | Swelling (mL/mL) |
|---|---|---|---|---|
| P1 | 70 | 0.076 | 5.3 | 1.9 |
| P$_N$1 | 247 | 0.24 | 4.3 | 1.2 |
| P2 | 208 | 0.22 | 3.8 | 1.8 |
| P$_N$2 | 342 | 0.66 | 3.8 | 1.9 |

The BET specific surface area (S), specific pore volume (V$_p$) and average pore diameter (D$_p$) were calculated from the nitrogen adsorption isotherms whereas the swelling in mL/mL was determined by soaking 1 mL of a packed bed of polymer particles in [MeCN/water 90/10 (v/v)+1% Et$_3$N] as described in the experimental section.

TABLE 3

Elemental composition of Fmoc-pTyrOMe imprinted and non-imprinted polymers

| Polymer | % C Calc. | % C Found | % H Calc. | % H Found | % P Calc. | % P Found | % O Calc. | % O Found | % N Calc. | % N Found | % F Calc. | % F Found |
|---|---|---|---|---|---|---|---|---|---|---|---|---|
| P1 | 60.3 | 58.2 / 67$^a$ | 7.7 | 7.4 | 0.316 | 0.010 | 28.4 | 28.3$^a$ | 1.86 | 1.72 / 1.80$^a$ | 2.33 | 2.65$^a$ |
| P$_N$1 | 60.0 | 57.5 / 67$^a$ | 7.0 | 7.3 | 0 | 0 | 28.8 | 28.6$^a$ | 1.80 | 1.92 / 1.93$^a$ | 2.40 | 2.57$^a$ |
| P2 | 61.4 | 59.0 | 7.1 | 7.4 | 0.327 | n.d | 29.3 | n.d | 1.90 | 1.93 | 0 | n.d. |
| P$_N$2 | 61.0 | 58.2 | 7.0 | 7.1 | 0 | n.d | 30.2 | n.d | 1.80 | 1.97 | 0 | n.d. |

$^a$Mass concentration obtained by XPS.

Thus, all polymers except P1 exhibited a mesoporous morphology with surface areas larger than 200 m$^2$/g and an average pore diameter of roughly 4 nm. This contrasted with P1 which showed a much lower surface area and pore volume but on the other hand which exhibited a higher swelling factor than the other materials. This result may be rationalized as follows. In P1 the template acts as a "glue" between two molecules of 1, causing the resulting complex to act as a virtual cross-linking monomer. P$_N$1 on the other hand is formed from non-complexed 1. This virtual difference in cross-linking levels may be the cause of the morphology differences observed. Such differences would not be expected for P2 and P$_N$2 since the latter involves templating a 1:1 complex.

Imprinting effects were thereafter assessed by chromatography using the crushed polymer monoliths as stationary phases. Our first goal was to investigate how well the polymers were able to discriminate the template from other amino acid derivatives containing side chains with an expected affinity for the urea motif as exemplified below by the Fmoc-protected amino acid esters.

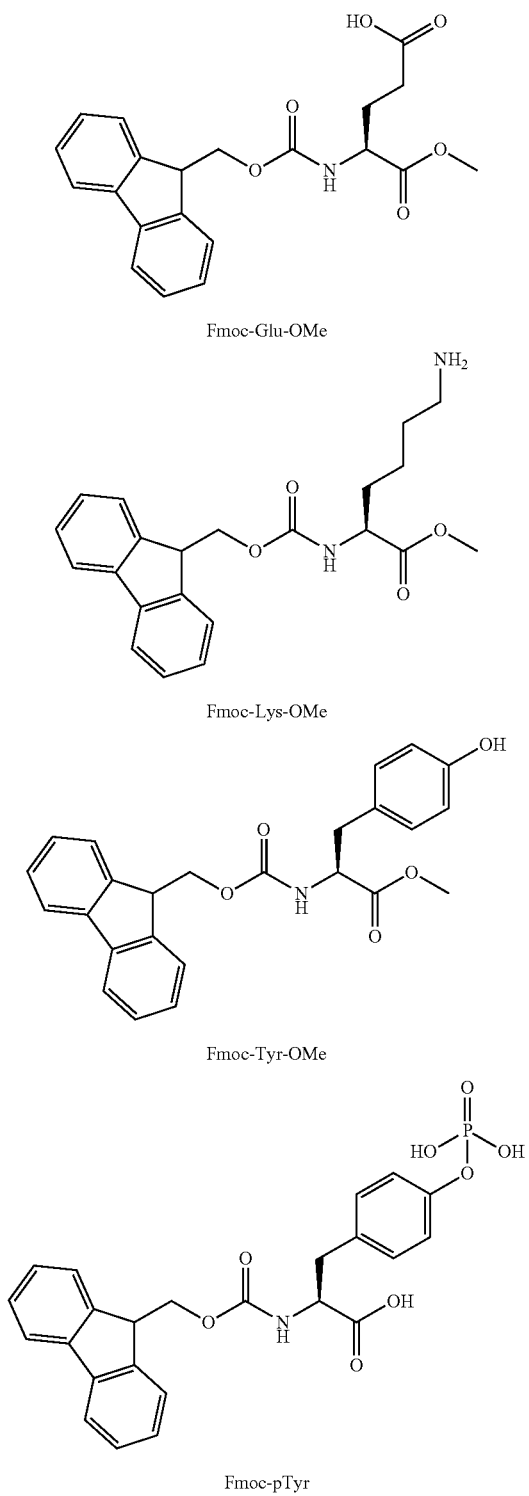

Fmoc-Glu-OMe

Fmoc-Lys-OMe

Fmoc-Tyr-OMe

Fmoc-pTyr

-continued

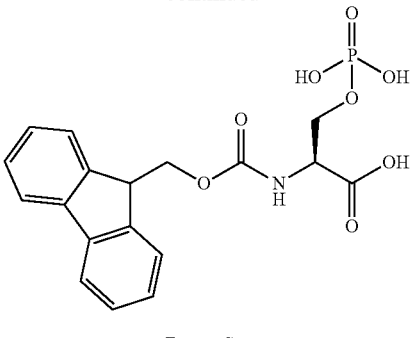

Fmoc-pSer

Thus, Fmoc amino acid methyl esters were injected on the columns in an acetonitrile rich mobile phase buffered with triethylamine and the retention factors can be seen in FIG. 3. Basic conditions were used in order to promote deprotonation of the template and thus to allow more stable quadruple hydrogen bonds to develop with the template. For P1 and $P_N1$ the mobile phase was: MeCN/water: 90/10 (v/v) (1% triethylamine) whereas for P2 and $P_N2$ it was: MeCN/water: 93/7 (v/v) (1% triethylamine). Stock solutions of each analyte (5 μL of 0.5 mM solutions in acetonitrile) were injected at a flow rate of 1 mL/min and a detection wave length of 260 nm. Conditions: 4.5×125 mm column, DAD λ=260 nm, Flow rate=1 mL/min, Inj. Vol.=20 μL.

Figure 4:
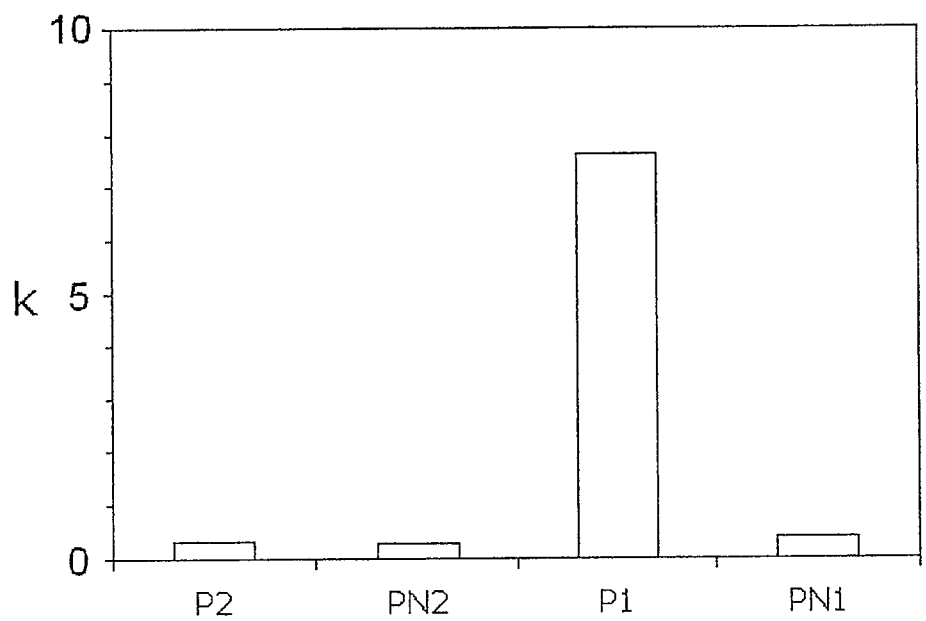

FIG. 4 discloses retention factor for Fmoc-pTyrOMe using MeCN/[potassium phosphate buffer, 0.02M, pH7]: 50/50 (v/v) as mobile phase. Conditions were otherwise as above.

Thus, whereas FIG. 3 shows that P1 and P2 exhibited strong affinity for the template Fmoc-pTyrOMe, the other amino acids were only weakly retained. $P_N1$ and $P_N2$, on the other hand, exhibited no affinity for any of the control analytes under these conditions. P1 exhibited stronger template retention than P2 and these differences were magnified when assessing the polymers in a phosphate-buffered mobile phase (FIG. 4). Under these conditions, only P1 retained the template, with a retention factor close to 10, whereas breakthrough was seen on P2. The fact that P1 still retains the template to a significant extent reflects the tight complex formed between 1 and Fmoc-pTyrOMe. These data are corroborated by the relative stabilities of the complexes obtained from the NMR titrations (Table 1) and the modelling results, taking into consideration the somewhat more competitive solvent used when preparing P2.

Figure 5:
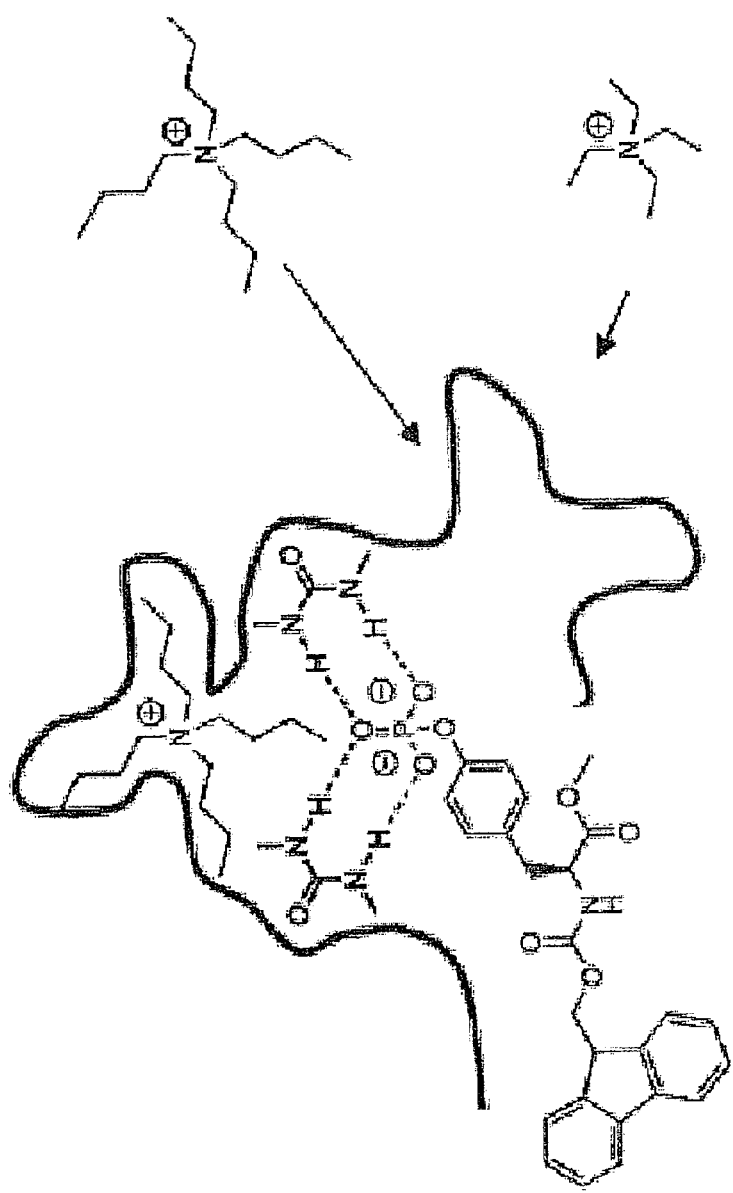

The binding energy distribution of the polymers versus the template was obtained from single-component adsorption isotherms determined by staircase frontal analysis.[12] Here, a mobile phase modified with an ion pair reagent (IPR) (Scheme 1) gave the largest slope and hence the highest template binding capacity while giving the lowest non-specific binding as judged from the binding of the template to the non-imprinted polymer. The effect depended on the size of the IPR with the strongest increase in selectivity observed for an IPR identical to the one used in the imprinting step. The end result is a strong imprint-related capacity increase. This suggests that both template components used in the imprinting step are required for efficient access to the imprinted sites (FIG. 5).

The Scatchard plots of the isotherms gave evidence for the existence of strong binding sites, in particular using a basic mobile phase (MeCN/[sodium carbonate (10 mM), pH 9.8]: 20/80 (v/v) a where we estimated binding constant values in excess of $10^7$ $M^{-1}$. Since these results were obtained using a water rich mobile phase (80% water) a comparison of the affinities with those observed for antibodies ellicited to react with phosphotyrosine seems justified. The latter exhibited binding affinities under optimal conditions in the range $10^6$-$10^7$ M$^{-1}$ which leads to the conclusion that the synthetic (MIP) and biological (antibody) receptors bind phosphotyrosine with similar strengths.

Crucial to the utility of the reported imprinting strategy would be to what extent these pTyr-selective sites would cross-react with peptides containing this epitope. This is far from evident given the size of the template and the lack of pore system control in conjunction with the imprinted sites. For instance, microporous materials would effectively exclude oligopeptides on the basis of their size. However, the wide pore size distribution commonly observed in imprinted polymers reduces the question to: how many of these sites are associated with larger pores allowing access to the larger target peptides?

Figure 6:
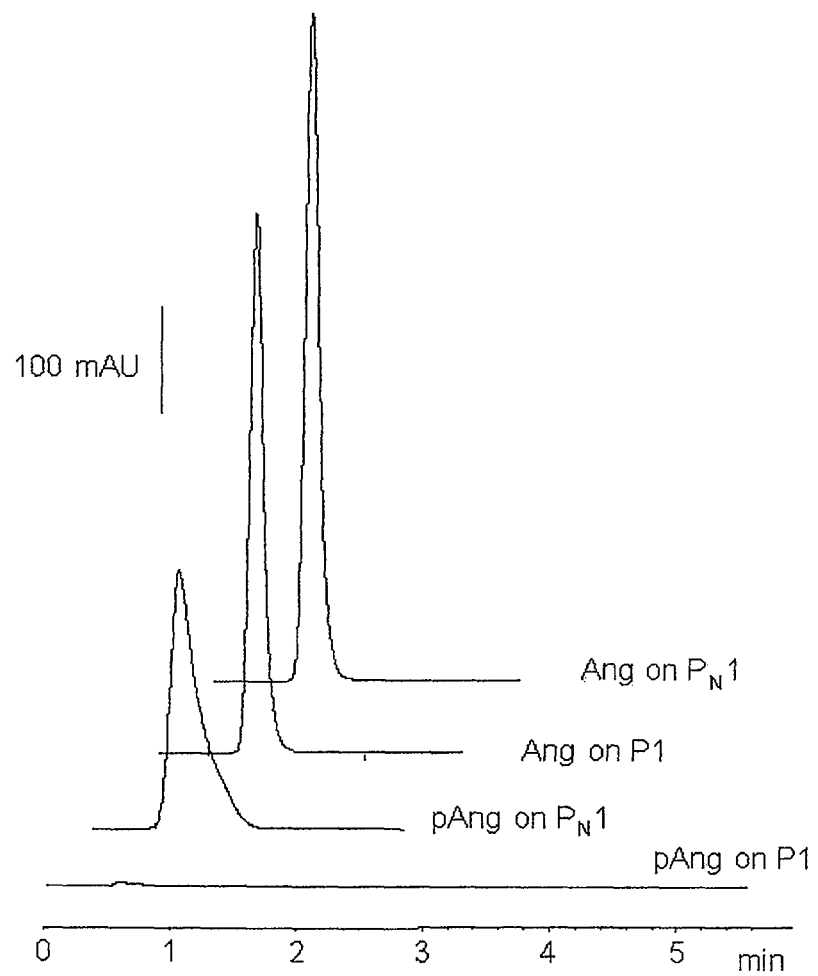
FIG. 6 illustrates elution profiles of Angiotensin (Ang) and p-Angiotensin (pAng) injected on P1 and $P_N1$

An answer to this question was provided by the use of a small set of test peptides available in the mono- and non-phosphorylated forms and including both tyrosine and serine residues as phosphorylation sites (Table 4).

p-Ang also breaks through completely, but only on $P_N1$ and with the exception of water poor mobile phases, where some retention is observed. P1 retains the phosphorylated peptide selectively and mainly in water poor and water rich mobile phases. In the case of the latter systems, using a mobile phase containing 80% water, an example is shown in FIG. 6 where Elution profiles of Angiotensin (Ang) and p-Angiotensin (pAng) are shown, injected on P1 and $P_N1$ as indicated using MeCN/water 20/80 (v/v) (0.1% TFA) as mobile phase. Reconditioning was performed using MeOH (0.1% TFA) instead of MeOH. Whereas pAng appears almost quantitatively retained on P1, it breaks through on $P_N1$. Meanwhile Ang breaks through completely on all columns.

The selectivity of P1 for pAng was also investigated by MALDI-TOF MS analysis of fractions collected prior to and after the switch from mobile phase A to the eluting mobile phase B. We here chose to focus on the water poor mobile phase A (MeCN/water: 95/5) showing low non specific hydrophobic binding and high pAng selectivity. The angiotensin peptides exhibited minor fragmentation in the MALDI experiment and appeared as peaks agreeing with the molecular masses of the parent peptides. This allows rough estimates

TABLE 4

Tyrosine and serine containing model peptides used to probe the phosphoselectivity of the polymers.

| Peptide name | Nonphosphorylated | Phosphorylated |
| --- | --- | --- |
| ZAP70 | ALGADDSYYTAR | ALGADDSpYYTAR |
| Angiotensin (Ang) | DRVYIHPF | DRVpYIHPF |
| Ser-436 | CDFRSFRSVT | CDFRpSFRSVT |
| Ser-357 | AHRHRGSARLHPPLNHS | AHRHRGpSARLHPPLNHS |
| pThr-295 | — | SQVGLpTRRSRTE |

The phosphorylated peptides are indexed by the letter p preceding the abbreviation e.g. pAng for phosphorylated angiotensin, pT for phosphorylated threonine and pS for phosphorylated serine.

The first evidence for phosphopeptide selectivity was obtained when investigating the ZAP70 model peptides in water poor mobile phases. With 0.1% TFA as an acidic mobile phase modifier, the difference in retention between P1 and $P_N1$ for this peptide became evident when reducing the water content in the mobile phase.

At 20% water the non-phosphorylated and phosphorylated peptides coeluted near the void marker, while at 10% water the phosphorylated peptide eluted as a broad, strongly tailing band, whereas breakthrough was still seen on $P_N1$.

Due to the scarcity of this peptide we then turned to investigate the retention of another tyrosine peptide, angiotensin, present in both non-phosphorylated (Ang) and monophosphorylated (pAng) forms. In order to better understand the retention mechanism of these peptides they were injected on P1 and $P_N1$ using a series of TFA modified binary acetonitrile:water mobile phase mixtures. The sometimes strong retention of the peptides and their weak UV-chromophores precluded accurate measures of retention times and we decided to instead record the portion of total peptide injected that eluted with minor retention within the first 10 minutes after injection. In order to avoid carry over effects due the strong retention, the columns were regenerated after each run using a stronger elution solvent.

A strong phosphopeptide preference was evident, as seen in the large difference in the % eluted peptide when comparing the two peptide forms. Ang was poorly retained on both polymers, except in water rich mobile phases (>80% water), where hydrophobic nonspecific binding becomes prevalent.

of the peptides contents in each fraction from the relative peak intensities. Thus Ang is fully recovered in mobile phase A on both columns whereas pAng is selectively retained on P1. The question is to what extent pAng can be recovered once adsorbed. Evidence for this was obtained using a somewhat stronger eluting mobile phase B (MeOH 0.1% TFA) resulting in elution of pAng from P1 but not from $P_N1$. The lower intensity of the peak in this case would suggest that pAng is not fully recovered. However, an accurate mass balance requires an accurate quantitative measurement of the peptides but unfortunately, MALDI can at the most give estimates of their relative abundance.

Having established selectivity of P1 for a phosphorylated versus a non-phosphorylated peptide we turned to investigate wether the receptors could discriminate between pTyr and pSer containing peptides. For this purpose we performed measurement of the breakthrough fractions of the Ser containing reference peptides Ser-436 and pSer-436 in analogy with the experiment performed for Ang and pAng. The results were in contrast to the results obtained for the pTyr peptide Angiotensin, in showing no evidence for a phosphate-related selectivity. Thus Ser-436 and pSer-436 behave seemingly in an identical manner on both P1 and $P_N1$ generally resulting in somewhat lower recoveries at both high and low aqueous contents when compared with the Angiotensin results.

Figure 7:
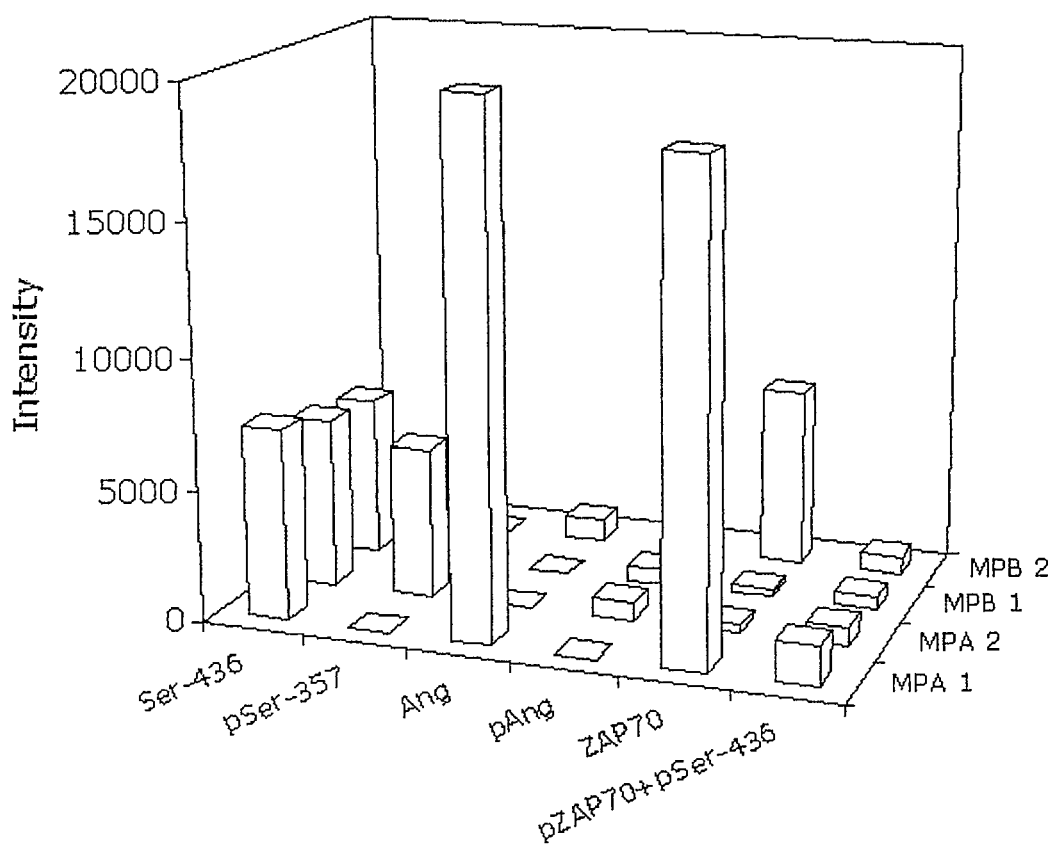
FIG. 7 illustrates MALDI MS analysis of fractions collected with 5 minute intervals after injection of 10 μL of a model peptide mixture on P1.
Figure 8:
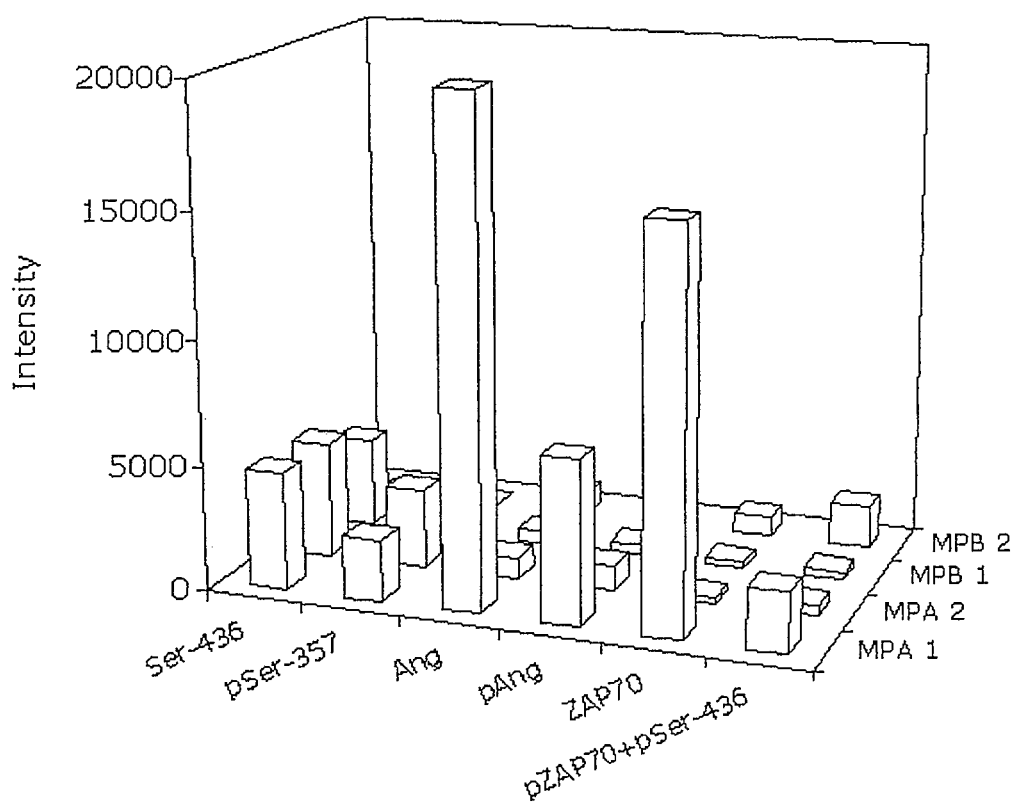
FIG. 8 illustrates MALDI MS analysis of fractions collected with 5 minute intervals after injection of 10 μL of a model peptide mixture on $P_N1$.

Although encouraging, the results so far discussed are based on separate injections of the peptide analytes and may not reflect the ability of the polymer to enrich phosphorylated peptides from peptide mixtures. In order to test the usefulness of the polymers in solid phase extraction, model peptide mixtures containing the nine peptides shown in Table 4 were prepared. In addition to an equimolar mixture of all peptides we prepared a mixture containing the pTyr peptides pZAP70 and pAng at a 100 fold lower concentration than the non pTyr peptides. This was done in an attempt to approach the more realistic conditions one would expect in tryptic digests, such as multi-peptide tryptic digests. FIGS. 7 and 8 show 3D graphs from the latter experiment depicting the MALDI peak intensities for the peptides in the different fractions collected (two fractions from MP A and two from MP B). Interestingly, the pTyr selectivity is observed also when extracting from the more complex mixture. Thus whereas the non-phosphorylate peptides or those phosphorylated at Ser or Thr exhibit no clear difference in their behaviour on P1 and $P_N1$, pAng is again selectively captured by P1. Thus in the first MP A fraction from P1, no pAng is detected which contrasts with the finding of pAng in the corresponding fraction after $P_N1$ extraction. Concerning pZAP70, this peptide unfortunately gave rise to a mass peak coinciding with that of pSer-436 thus precluding separate identification of these peptides. Nevertheless, the lower intensity observed for the $M^+$ peak in the first MP A fraction of P1 compared to that of $P_N1$ may again be the result of a pTyr preference. Taken together, the above results show that P1 can be used for selective enrichment of pTyr peptides from peptide mixtures.

MALDI MS analysis of fractions are collected with 10 minute intervals after separate injection of Ang or pAng on P1 or $P_N1$ using the loading mobile phase A (Load) and after switch to an eluting mobile phase B (Elute). MALDI MS analysis of fractions are collected with 5 minute intervals after injection of 10 µL of a model peptide mixture on P1 (A) or $P_N1$ (B) using a loading mobile phase A (Load) and after switch to an eluting mobile phase B (Elute). The peptide mixture consisted of the nine peptides in Table 4 each at a concentration of 11 µg/mL except for pAng and pZAP70 which were present at a concentration of 0.11 µg/mL in mobile phase A. Mobile phase A=MeCN/water: 95/5 (v/v) (0.1% TFA). Mobile phase B=MeOH (0.1% TFA).

The results show that combinations of binding motifs from host guest chemistry with conventional imprinting may be very rewarding. Thus the stable complexes formed from diarylurea host monomers and quarternary ammonium phosphate salts results in exceptionally tight binding sites when imprinted. With binding constants for the amino acid template exceeding $10^7$ $M^{-1}$ in a aqueous rich solvent (80% water) the pTyr imprinted polymers compare favorably to pTyr-antibodies which display upper affinities in the $10^6$-$10^7$ $M^{-1}$ range. The nature of the binding site could be deduced from NMR titrations and molecular modelling experiments. These all suggested the formation of tight complexes between two diarylurea monomers and one phosphate group via quadropole hydrogen bonding aided by a π-π interaction between one of the monomer ligands and the tyrosine phenyl group.

The sites exhibit sufficient binding energy to bind shorter peptides containing phosphorylated tyrosine whereby the templating induces clear phosphotyrosine selectivity. The ability of these sites to discriminate between pSer and pTyr containing shorter peptides as well as the apparently small charge dependent sequence bias seem promising for future applications of the polymers as robust and generic pTyr selective SPE phases. The approach also appears suited for the design of sequence specific phases for instance targeting disease biomarkers or for more advance peptide fractionation.

The above mentioned synthetic receptors (MIPs) could be incorporated in sensors where the binding event would be translated into a measurable signal. For instance, binding can give rise to a change in colour or luminescence of a receptor which could be easily measured. Alternatively, such receptors if prepared in soluble or nanoparticulate form could be used as therapeutic agents e.g. for depletion of phosphorylated peptides or proteins from biological fluids or for modulating a biological activity such as inhibiting dephosphorylation events or as imaging agents provided that the receptor contains a visible label. In this context, therapy may also involve the use of soluble or non-soluble imprinted receptors for extraction, separation or depletion of phosphorylated peptides or proteins from biological fluids e.g. based on apheresis or as oral adsorbers as well as using the receptor for modulating a biological activity.

DEFINITIONS

As used in the present invention, the term "isosteric" means a group exhibiting similarities in its chemical and/or physical properties.

As used in the present invention "phosphate groups" means any phosphate covalently linked to another moiety. For example, a phosphate of the present invention would include phosphorylated tyrosine or peptides or proteins containing phosporylated tyrosine, but exclude sodium dihydrogen phosphate.

As used in the present invention, the term "epitope" means the part of a macromolecule, such as a protein, polysaccharide or a nucleic acid, that is recognized by the molecularly imprinted polymer.

As used in the present invention, the term "decorated" means that a molecule, such as a oligomer or a polymer, is covalently linked to the molecule, such as a template.

As used in the present invention, the term "N,O protected phosphotyrosine" or "N and/or O-protected phosphotyrosine" means that the amino acid is protected on the α-amino and/or α-carboxylic acid groups.

Examples

The invention will now be described in more detail with reference to a number of non-limiting examples:
Materials Phosphoroxytrichloride ($POCl_3$), N-methylmorpholine (NMM), 1-naphtyldihydrogenphosphate (NP), tetraethyl ammonium tetrafluoroborate (TEATFB), and ethylene glycol dimethacrylate (EDMA) were obtained from Aldrich (Milwaukee, USA), toluene from Fischer (Zurich, Switzerland) 1,2,2,6,6-pentamethylpiperidine and methacrylic acid (MAA) from Fluka (Buchs, Switzerland), 2,2-diphenyl-1-picrylhydrazyl (DPPH) from Sigma, dimethylformamide (DMF) from Riedel-deHaën (Seelze, Germany), 2,2'-azobisisobutyronitrile (AIBN) from SERVA (Heidelberg, Germany), acetonitrile and methanol from J. T. Baker (Phillipsburg, N.J., USA). N,N'-azo-bis(2,4-dimethyl)valeronitrile (ABDV) was purchased from Wako. EDMA was purified by the following procedure prior to use: The received material was washed consecutively with 10% aqueous NaOH, water, brine and finally water. After drying over $MgSO_4$, pure, dry EDMA was obtained by distillation under reduced pressure. All other reagents were used as received. DMSO-$d_6$ was purchased from Deuterio-GmbH (Kastellaun, Germany). Anhydrous solvents, dichloromethane and tetrahydrofuran, were stored over appropriate molecular sieves. Other solvents were of reagent grade or higher.

The functional monomers N-3,5-bis(trifluoromethyl)phenyl-N'-4-vinylphenyl urea (1), 1,1'-(1,3-phenylenebis(methylene))bis(3-(4-vinylphenyl)urea) (2), and the substrates Fmoc-Tyr-OMe (Adamson, J. G., *J. Org. Chem.* 1991, 56, 3447-3449), Fmoc-Glu-OMe (*J. Org. Chem.*, Vol. 67, N° 14, 2002) and Fmoc-Lys-OMe (*J. Am. Chem. Soc.*, Vol. 118, N° 42, 1996) were synthesised as described elsewhere whereas the analytes Fmoc-pSer-OH and Fmoc-pTyr-OH were purchased from Bachem.-GmbH (Weil am Rhein, Germany) The peptide angiotensin and phospho-angiotensin were obtained from Calbiochem-Merck (Darmstadt, Germany), the ZAP70 peptides and the reference peptides Ser-436, pSer-436, Ser-357, pSer-357 and pThr-295 were obtained as generous gifts from Prof. Rainer Bischoff (University of Groningen, NL) (ZAP70) and P. D. Dr. Rainer Lehmann (University Hospital Tubingen, Germany) respectively.

Apparatus and Methods.

HPLC measurements were carried out on Hewlett-Packard HP 1050 or 1100 instruments (Agilent Technology, Waldbronn, Germany).

Elemental analysis were performed at the Department of Organic Chemistry, Johannes Guttenberg Universität Mainz using a Heraeus CHN-rapid analyser (Hanau, Germany).

FT-IR spectroscopy was performed using a NEXUS FT-IR spectrometer (Thermo Electron Corporation, Dreieich, Germany).

Nitrogen sorption measurements were performed on a Quantachrome Autosorb 6B (Quantachrome Corporation, Boynton Beach, Fla.) automatic adsorption instrument. Prior to measurements, 100-150 mg of the samples was heated at 40-60° C. under high vacuum ($10^{-5}$ Pa) for at least 12 hours. The specific surface areas (S) were evaluated using the BET method, the specific pore volumes ($V_p$) following the Gurvitch method and the average pore diameter ($D_p$) using the BJH theory applied to the desorption branch of the isotherm.

Measurement of swelling: NMR tubes were filled during intermittent vibrations up to 1 cm (142 μL) with dry polymer particles (MIPs and NIPs) and were thereafter weighed. Solvent (1 mL) was added and the particles allowed to equilibrate in the solvent for 24 h, whereafter the volume of the swollen particles was measured. The following solvents were employed: Acetonitrile, Toluene, 0.01 M Sodium Acetate Buffer (pH=4.8) and Cyclohexane.).

Matrix assisted laser desorption ionization (MALDI) mass spectrometry: These experiments were carried out on a MALDI-TOF mass spectrometer. The instrument was operated in the reflection mode for all analyses except for the positive/negative ion comparative study, which were carried out in the linear mode. The analysis method was RPMixt Par.

1-(4-Vinylphenyl)-3-(3,5-bis(trifluromethyl)phenyl)-thiourea (3)

To a stirred solution of 4-aminostyrene (3.5 mmol) in dry THF (20 mL) under nitrogen was added 3,5-bis-(trifluoromethyl)phenyl isothiocyanate (3.5 mmol). The solution was refluxed overnight and then the solvent was evaporated under reduced pressure. The resulting solid residue was purified by column chromatography to yield the desired product in 60% yield.

$^1$H NMR (DMSO-$d_6$): 5.22 (d, 1H), 5.28 (d, 1H), 6.76 (dd, 1H), 7.51 (s, 4H), 7.77 (m, 1H), 8.34 (s, 2H), 9.47 (s, 1H), 9.56 (s, 1H). $^{13}$C NMR (DMSO-$d_6$) 114.21, 117.18, 122.22, 123.7, 124.13, 124.24, 124.94, 126.87, 129.85, 130.17, 130.50, 130.82, 134.37, 136.33, 138.44, 142.04, 179.81. MS (FAB) m/z ($M^+$) 390.0, ($[M+H]^+$) 391.0. Calculated for C17H12F6N2S: C, 52.31; H, 3.10; N, 7.18; S, 8.21. Found: C, 52.19; H, 3.14; N, 7.22; S, 8.25.

N-(9-fluorenylmethoxycarbonyl)-O'-phosphonotyrosine-methyl ester (Fmoc-pTyrOMe)

The synthesis of Fmoc-pTyrOMe followed a previously reported procedure starting from Fmoc-Tyr-OMe (Krog-Jensen, C., Fmoc-ptyrome, *Letters in Peptide Science* 1999, 6, 193-197).

To 3.00 g (7.186 mmol) Fmoc-Tyr-OMe in 75 mL dry dicloromethane 2.20 g=1.34 mL (14.373 mmol) phosphoroxychloride and 0.87 g=0.95 mL (8.624 mmol) N-methylmorpholine were added and the solution was stirred for 3 h whereby the conversion was monitored by TLC (chloroform/acetone 19:1). Another 0.5 mL POCl$_3$ and 0.4 mL NMM were added and the solution stirred for another 4 h. The organic phase was washed twice with 1N HCl solution, once with water and evaporated. The residue was taken up in 20 mL acetone and 2 mL stirred for 5 min and evaporated. This was repeated 3 times. The product was purified by column chromatography twice (chloroform/methanol 9:1+1% acetic acid). Yield: 2.13 g (61.3%). The purity was estimated by reversed phase HPLC to ~95% based on peak areas (column: C-18 Luna, mobile phase: 50% (acetonitril-1% triethylamine)-50% water, UV: 254 nm). Elemental analysis for dihydrated complex: Calculated: C, 56.3; H, 5.29; N, 2.63. Found: C, 56.7; H, 5.15; N, 2.75. $^1$H-NMR (DMSO-$d_6$) 2.75-3.10 (m 2H), 3.6 (s 4H), 4.1-4.3 (m 4H), 7.0-8.0 (m 12H). $^{31}$P-NMR (DMSO-$d_6$) −1.523 (s PO$_4^-$). FAB [M−H]$^-$ 496.16.

Bis-tetrabutylammonium phosphate Salts

Bis-tetrabutylammonium naphthalen-1-yl phosphate (TBA$_2$NP): To 0.50 g (2.231 mmol) naphtyl-1-phosphate in 10 mL dry methanol 4.46 mL of a 1 M solution of tetrabutylammonium hydroxide in methanol (2 eq.) was added and the solution stirred at room temperature for 2 h. The solvent was removed under vacuum and the residue dried over P$_2$O$_5$. The bis-tetrabutylammonium salt of the template Fmoc-pTyrOMe was synthesised in a similar manner.

Tetrabutylammonium naphthalen-1-yl hydrogenphosphate (TBANHP)

To 0.50 g (2.231 mmol) naphthyl-1-phosphate in 10 mL dry methanol. 2.23 mL of a 1 M solution of tetrabutylammonium hydroxide in methanol (1 eq.) were added and stirred at room temperature for 2 h. The solvent was removed and the residue dried over P$_2$O$_5$.

Polymer Preparation

Imprinted polymers P1 and P2 were prepared in the following manner. The bis-tetrabutylammonium salt of Fmoc-pTyrOMe (template) (0.5 mmol), urea monomer (P1: 1 mmol 1; P2: 0.5 mmol 2), methacrylamide (4 mmol) and EDMA (20 mmol) were dissolved in THF (P1) or DMF (P2) (5.6 mL). To the solution was added initiator ABDV (1% w/w of total monomers). The solution was transferred to a glass ampoule, cooled to 0° C. and purged with a flow of dry nitrogen for 10 minutes. The tubes were then flame-sealed while still under cooling and the polymerization initiated by placing the tubes in a thermostat controlled water bath pre-set at 50° C. After 24 h the tubes were broken and the polymers lightly crushed. They were thereafter washed 3 times with MeOH/0.1N HCl 1:1 and extracted in a Soxhlet-apparatus with methanol for 24 h. This was followed by further crushing and sieving, whereby the fraction from 25-36 μm was used for packing the HPLC-columns to evaluate their binding properties. A non-imprinted polymer (P$_N$#) was prepared in the same way as described above, but with the omission of the template molecule from the pre-polymerisation solution.

HPLC Evaluation

The 25-36 μm particle size fraction was repeatedly sedimented (80/20: methanol/water) to remove fine particles and then slurry-packed into HPLC columns (30 mm×4.6 mm i.d. or 50 mm×4.6 mm) using the same solvent mixture as pushing solvent. Subsequent analyses of the polymers were performed using an Agilent HP1050 or HP1100 system equipped with a diode array-UV detector and a workstation. Analyte detection was performed at 260 and 220 nm, depending on the analyte, and at a flow rate of 0.5 mL/min. The retention factor (k) was calculated as $k=(t-t_0/t_0)$, where t=retention time of the analyte, $t_0$=retention time of the void marker (acetone or sodium nitrate).

Solid Phase Extraction

MISPE experiments were performed off line using HPLC columns (30 mm×4.6 mm i.d.) packed with P1 and $P_N1$ and manual fraction collection at the detector outlet. The hardware consisted in an Agilent HP 1050 system equipped with a binary pump, a diode array-UV detector and workstation. Analyte detection was performed at 260 and 220 nm, depending on the analyte, and at a flow rate of 0.5 mL/min. The MISPE experiments comprised a conditioning step using the loading solvent A, a loading step also using the loading solvent A and an elution step using a stronger eluent (B). Loading consisted in injecting 10 μL of single peptides or a peptide mixture and then passing the load solvent through the column for a given time. Either one or two fractions were collected in the load and elution steps.

MALDI-TOF Mass Spectrometric Analysis

Materials: 2,5-dihydroxybenzoic acid (DHB), α-cyano-4-hydorxy-cinnamic acid (CHCA), Phosphoric acid, Methanol.

Matrix-assisted laser desorption ionization mass spectroscopy (MALDI) experiment were carried on MALDI-TOF mass spectrometer, equipped with laser. The instrument was operated in the reflection mode for all analyses except for positive/negative ion comparative study, which were carried out in linear mode. For MALDI study, the analysis method was chosen as RPMixt Par.

The sample was spotted directly onto target plate for MALDI-MS analysis. The 2,5-dihydroxybenzoic acid (DHB), α-cyano-4-hydorxy-cinnamic acid (CHCA) was chosen as a matrix for phosphorylated and non-phosphorylated peptide respectively. μl of matrix and μl of sample were mixed on target plate by using micropipette and dried at room temperature. For the peptide mixture analysis, the samples were evaporated to dryness under vacuum at room temperature. These samples were redissolved in 200 μL of 1.35% phosphoric acid in methanol by mere shaking and sonicated for 5 min. For the peptide mixture, 1 μl of DHB matrix and 1 μl of this prepared sample were mixed on target plate by using micropipette and dried at room temperature. All MALDI-MS data were manually acquired with each detected peak assigned manually.

(1) Turner, N. W.; Jeans, C. W.; Brain, K. R.; Allender, C. J.; Hlady, V.; Britt, D. W., From 3d to 2d: A review of the molecular imprinting of proteins, *Biotechnol. Prog.* 2006, 22, 1474-1489.

(2) Titirici, M. M.; Hall, A. J.; Sellergren, B., Hierarchical imprinting using crude solid phase peptide synthesis products as templates, *Chemistry of Materials* 2003, 15, 822-824.

(3) Nishino, H.; Huang, C.-S.; Shea, K. J., Selective protein capture by epitope imprinting, *Angewandte Chemie, International Edition* 2006, 45, 2392-2396.

(4) Manesiotis, P.; Hall, A. J.; Emgenbroich, M.; Quaglia, M.; de Lorenzi, E.; Sellergren, B., An enantioselective imprinted receptor for z-glutamate exhibiting a binding induced color change, *Chem. Commun.* 2004, 2278-2279.

(5) Urraca, J. L.; Hall, A. J.; Moreno-Bondi, M. C.; Sellergren, B., A stoichiometric molecularly imprinted polymer for the class-selective recognition of antibiotics in aqueous media, *Angew. Chem. Int. Ed.* 2006, 45, 1-5.

(6) Fan, E.; Van Arman, S. A.; Kincaid, S.; Hamilton, A. D., Moleclar recognition: Hydrogen bonding receptors that function in highly competitive solvents, *J. Am. Chem. Soc.* 1993, 115, 369-370.

(7) Esteban Gomez, D.; Fabbrizzi, L.; Licchelli, M.; Monzani, E., Urea vs. Thiourea in anion recognition., *Org. Biomol. Chem.* 2005, 3, 1495-1500.

(8) Etter, M. C.; Panunto, T. W., 1,3-bis(m-nitrophenyl)urea: An exceptionally good complexing agent for proton acceptors., *J. Am. Chem. Soc.* 1988, 110, 5896-5897.

(9) Hall, A. J.; Manesiotis, P.; Emgenbroich, M.; Quaglia, M.; De Lorenzi, E.; Sellergren, B., Urea host monomers for stoichiometric molecular imprinting of oxyanions, *Journal of Organic Chemistry* 2005, 70, 1732-1736.

(10) Connors, K. A. *Binding constants. The measurement of molecular complex stability*; John Wiley & Sons: New York, 1987.

(11) Bühlmann, P.; Nishizawa, S.; Xiao, K. P.; Umezawa, Y., Strong hydrogen bond-mediated complexation of $H_2PO_4^-$ by neutral bis-thiourea hosts., *Tetrahedron* 1997, 53, 1647-1654.

(12) Sajonz, P.; Kele, M.; Zhong, G.; Sellergren, B.; Guiochon, G., Study of the thrmodynamics and mass transfer kinetics of two enantiomers on a polymeric imprinted stationary phase, *J. Chromatogr.* 1998, 810, 1-17.

The invention claimed is:

1. A method of separating or extracting a peptide or protein containing phosphorylated tyrosine comprising
providing a molecularly imprinted polymer obtainable by
providing at least one monomer exhibiting affinity for phosphate groups, at least one template, and at least one cross-linker, wherein the template is a N and/or O protected phosphotyrosine or a quaternary ammonium salt thereof, wherein said monomer is selected from

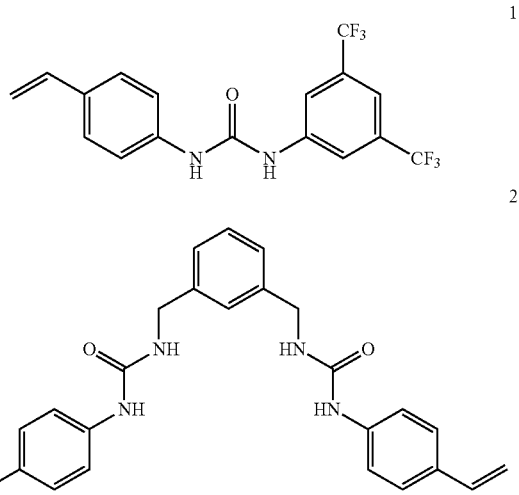

forming a pre-polymerization mixture,
polymerizing said pre-polymerization mixture; and
removing the template by washing to yield a molecularly imprinted polymer having a cavity complementary to said template;
contacting the resulting molecularly imprinted polymer with a mixture comprising at least one peptide or protein or any mixture thereof comprising phosphorylated tyrosine that is captured in the cavity of the molecularly imprinted polymer.

2. A method according to claim 1, additionally comprising releasing said captured phosphorylated peptide or protein from said molecularly imprinted polymer.

3. A method according to claim 1, wherein the mixture contains two or more peptides, proteins or a mixture thereof.

4. A method according to claim 3, wherein at least one peptide or protein is phosphorylated and at least one peptide or protein is non-phosphorylated.

5. A method according to claim 1, wherein a phosphorylated peptide or protein is selectively extracted or separated over other phosphorylated or non-phosphorylated peptides or protein.

6. A method according to claim 1, wherein a peptide or protein phosphorylated on the phosphotyrosine side chain is selectively extracted or separated over peptides or proteins with other phosphorylated or non-phosphorylated amino acid side chains.

7. A method according to claim 1, wherein the peptides or proteins containing phosphorylated tyrosine are selectively separated or extracted over phosphorylated or non-phosphorylated peptides or proteins containing phosphorylated or non-phosphorylated serine and/or phosphorylated or non-phosphorylated peptides or proteins containing phosphorylated or non-phosphorylated threonine.

8. A method according to claim 1, wherein phosphorylated peptides or proteins in biological extracts or digests are separated or extracted.

9. A method according to claim 1, wherein the digests are selected from tryptic or other protease digests.

* * * * *